United States Patent [19]
Edell et al.

[11] Patent Number: 5,476,494
[45] Date of Patent: Dec. 19, 1995

[54] LOW PRESSURE NEURAL CONTACT STRUCTURE

[75] Inventors: David J. Edell, Lexington; Joseph Rizzo, III, Boston; John L. Wyatt, Jr., Sudbury, all of Mass.

[73] Assignee: Massachusetts Institute of Technology, Cambridge, Mass.

[21] Appl. No.: 234,725

[22] Filed: Apr. 28, 1994

Related U.S. Application Data

[63] Continuation of Ser. No. 943,513, Sep. 11, 1992, abandoned.

[51] Int. Cl.$^6$ ............................................................. A61B 5/04
[52] U.S. Cl. ........................... 607/116; 607/118; 623/24; 623/25; 128/642
[58] Field of Search ................... 623/24, 25; 128/642; 607/116, 118

[56] References Cited

U.S. PATENT DOCUMENTS

| | | | |
|---|---|---|---|
| 3,955,560 | 5/1976 | Stein et al. | |
| 4,026,300 | 5/1977 | DeLuca et al. | 623/24 |
| 4,551,149 | 11/1985 | Sciarra | |
| 4,628,933 | 12/1986 | Michelson | 128/784 |
| 4,878,913 | 11/1989 | Aebischer et al. | 623/12 |
| 4,932,405 | 6/1990 | Peeters et al. | |
| 5,016,633 | 5/1991 | Chow | 128/784 |
| 5,024,223 | 6/1991 | Chow | 128/784 |
| 5,109,844 | 5/1992 | de Juan, Jr. et al. | |

FOREIGN PATENT DOCUMENTS

WO90/00912 2/1990 WIPO.

OTHER PUBLICATIONS

Hawley's Condensed Chemical Dictionary, 11th Ed., 1987, p. 1040.

Wade G. Regehr et al., "A Long-Term In Vitro Silicon-Based Microelectrode-Neuron Connection", IEEE Transactions On Biomedical Engineering, vol. 35, No. 12, Dec. 1988.

*Primary Examiner*—Paul B. Prebilic
*Attorney, Agent, or Firm*—Choate, Hall & Stewart

[57] ABSTRACT

A low-pressure neural contact structure for contact with neural tissue, for example, neural tissue of the retina within which are ganglion cells to be electrically stimulated. The contact structure comprises a first portion for attachment to a first bodily location, such as the inner surface of the retina, and a second portion interconnected with the first portion via an interconnection and being held in contact with the neural tissue. The interconnection exhibits a weak restoring force which in conjunction with the geometry of said second portion provides a preselected desired pressure of contact against the neural tissue. As adapted for the retina, the interconnection exhibits a weak restoring force developed in response to curvature of the interconnection along the inner radius of the retina.

22 Claims, 2 Drawing Sheets

LOW PRESSURE NEURAL CONTACT STRUCTURE

This is a continuation of application Ser. No. 07/943,513 filed on Sep. 11, 1992 now abandoned.

BACKGROUND OF THE INVENTION

This invention relates to prosthetic devices for interfacing with neural tissue.

Neural tissue can be artificially stimulated and activated by prosthetic devices which pass pulses of electrical current through electrodes on such a device. The passage of current causes changes in electrical potentials across neuronal membranes which can initiate neuron action potentials, which are the means of information transfer in the nervous system. Based on this mechanism, it is possible to input information into the nervous system by coding the information as a sequence of electrical pulses which are relayed to the nervous system via the prosthetic device. In this way, it is possible to provide a variety of artificial sensations including touch, hearing, and vision for a variety of applications. It is also possible to monitor and record neural activity using such a scheme.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface. This placement must be mechanically stable, minimize the distance between the device electrodes and the neurons, and avoid undue compression of the neurons.

The retina is extraordinarily fragile. In particular, retinal neurons are extremely sensitive to pressure; they will die if even a modest intraocular pressure is maintained for a prolonged period of time. Glaucoma, which is one of the leading causes of blindness in the world, can result from a chronic increase of intraocular pressure of only 10 mm Hg. Furthermore, the retina, if it is perforated or pulled, will tend to separate from the underlying epithelium, which will eventually render it functionless. Thus attachment of a conventional prosthetic retinal electrode device is not practical, primarily because of the typically high pressures that such a device would exert on the retina, which would inevitably compromise the retinal neurons.

SUMMARY OF THE INVENTION

In general, in one aspect, the invention provides a low-pressure neural contact structure for contact with neural tissue. This structure features a first portion for anchoring to a bodily location, and a second portion interconnected with the first portion via an interconnection and contacting the neural tissue. The interconnection between the first and second portions exhibits a weak restoring force which in conjunction with the geometry of the second portion provides a preselected desired pressure of contact against the neural tissue. The invention is adaptable for any neural stimulation or sensing application in which neural tissue surface contact is required, and particularly where low-pressure neural contact is required. Furthermore, the structure provides the ability for attachment to neural tissue in a location distant from an active location, thereby isolating any physiological degradation due to the attachment. And of equal importance, the contact structure inherently provides adequate surface pressure for contacting neural tissue, while at the same time minimizing that pressure due to its ability to easily conform to contours in neural tissue.

In preferred embodiments of the invention, the second portion provides mechanical support for a stimulating electrode structure positioned on that portion for stimulating neurons within the neural tissue. The first and second portions may together comprise an integral structure, or in other embodiments, may comprise distinct structures. The integral structure is preferably of a homogeneous material and rectangular. More preferably, the integral structure is a silicon cantilever.

In other preferred embodiments, the neurons to be stimulated are autonomic nervous tissue associated with bladder function or neurons associated with activation of paretic limbs.

In still other preferred embodiments, the second portion comprises mechanical support for a transducing electrode structure positioned on the second portion for sensing neuronal activity, or for sensing chemical or physical parameters of the neural tissue. Preferably, the transducing electrode senses oxygen or temperature. In another preferred embodiment, the second portion provides mechanical support for a structure adapted to disperse chemicals into the neural tissue.

In general, in another aspect, the invention provides a low-pressure neural contact structure for contact with neural tissue of the retina within which are ganglion cells to be electrically stimulated. The invention features a first portion for attachment to a first location on the inner surface of the retina, and a second portion interconnected with the first portion via an interconnection and being held in contact with a second location on the inner surface of the retina adjacent to the ganglion cells to be stimulated. The interconnection exhibits a weak restoring force developed in response to curvature of the interconnection along the inner radius of the retina, whereby the weak restoring force, in conjunction with the geometry of the second portion, provides a preselected desired pressure of contact against the retinal neural tissue.

In preferred embodiments, the contact structure comprises a silicon cantilever; the second portion provides mechanical support for a stimulating electrode or array of electrode for stimulating the ganglion cells. Preferably, a layer of biocompatible encapsulation material encapsulates the cantilever; more preferably, the encapsulation material is silicone. The encapsulation material overhangs edges of the cantilever and is thicker in the location of the first portion than in the location of the second portion. The encapsulation layer preferably is perforated at the locations of the cantilever edges and provides channels located at positions corresponding to the positions of electrodes on the cantilever.

In other preferred embodiments, the cantilever is between 2–40 μm-thick, 2 mm–5 cm-long, and 0.5 mm–1 cm-wide, and the encapsulation layer is between 5–25 mm-thick. In other embodiments, a silicone rib is positioned on the cantilever to bend the cantilever in a predetermined geometric shape. In still other embodiments, the width of the cantilever in the location of the first portion and in the location of the second portion is greater than the width of the cantilever in the location of the interconnection.

Thus, the contact structure provides both a neural tissue contacting surface and mechanical support for stimuli and sensory electronics and electrodes. The structure is applicable to a wide range of stimulation prosthetics for visual, auditory, and sensory systems. Most importantly, the invention achieves the ability to contact neural tissue using an attachment scheme that does not interfere with an area of tissue to be stimulated, and yet at the same time provides adequate contact pressure against that tissue.

DESCRIPTION OF A PREFERRED EMBODIMENT

Figure 1A:
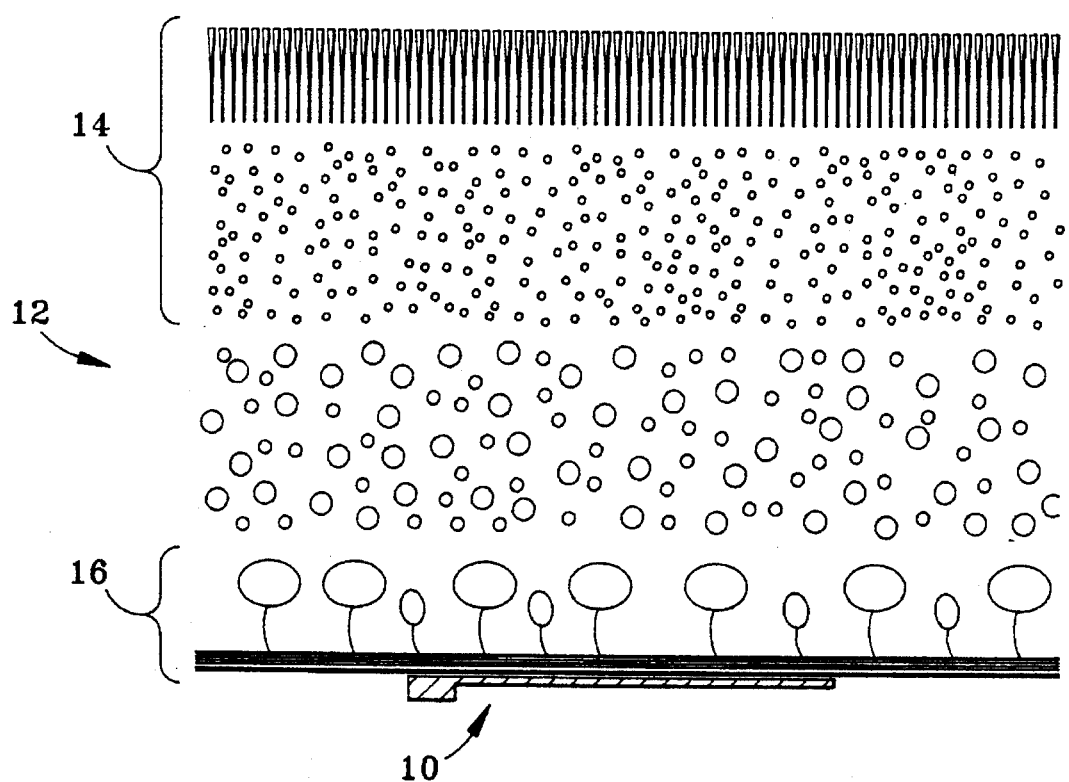
FIG. 1a is a view of the neural contact of the invention in place on the retina.
Figure 1B:
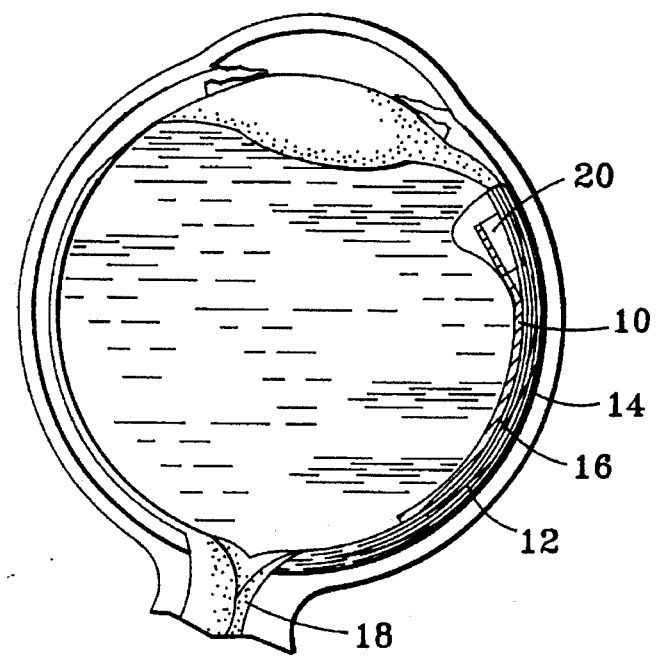
FIG. 1b is another view of the neural contact of the invention in place on the retina.

Referring to FIGS. 1a and 1b, there is shown the low-pressure neural contact of the invention 10 adapted for stimulation of retinal neural cells. As shown in the figure, the retina 12 consists of ten layers of cells. The outermost layers 14 (away from the geometric center of the eye) contain the rods and cones, which are the cells that sense the presence of light and initiate a nerve signal that passes to the brain. The innermost layers 16 (adjacent to the vitreous humor) primarily contain the ganglion cells, which have axons extending into the brain via the optic nerve 18. Between the inner and outer retinal layers are many different cell types that process neural signals from the rods and cones before the signals are sent to the brain. Light coming from the front of the eye must traverse the inner retina in order to reach the rods and cones. The corresponding signals generated by the rods and cones then travel to the inner retina on the way to the brain.

There are two types of retinal diseases which are of a nature which lends them to treatment via a retinal prosthetic implant positioned on the inner retinal surface using the neural contact of the invention. The first disease, macular degeneration, is the leading cause of blindness in the Western World: age-related macular degeneration affects approximately one in ten people over the age of 60 years. Visual loss due to this disease is progressive, and frequently causes loss in the "legal blindness" range. The pathology of macular degeneration affects the rods and cones, as well as a pigmented layer of cells upon which the rods and cones are aligned. However, the ganglion cells and their connections to the brain remain intact, and being located just below the inner surface of the retina, are opportunely located to be affected by electrical currents that are applied to the surface of the retina. A prosthetic retinal implant using the inventive contact may take advantage of this arrangement by being placed over and contacting the inner retinal surface for stimulation of those ganglion cells. In effect, this scheme bypasses the damaged area of the retina.

The other disease that is treatable with an implant using the inventive contact is retinitis pigmentosa. The cause of this inherited disease is not known, but the damage caused by the disease is also at the level of the rods and cones. Retinitis pigmentosa results in a progressive loss of vision over decades, leaving many sufferers almost totally blind. A medical treatment is not available for either retinitis pigmentesa or macular degeneration.

Figure 2A:
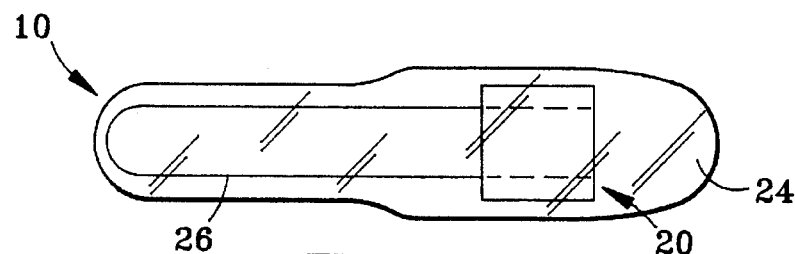
FIG. 2a is a planar view of one embodiment of the neural contact of the invention.
Figure 2B:
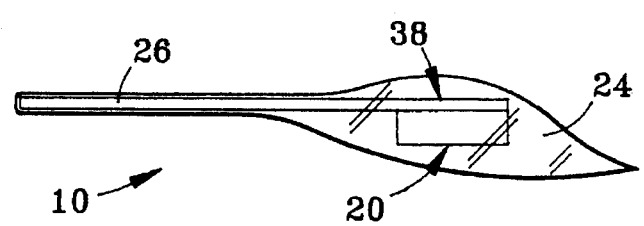
FIG. 2b is a side view of one embodiment of the neural contact of the invention.

Also referring to FIGS. 2a and 2b, the neural contact 10 consists of a thin cantilever which gently conforms to the curvature of the retina while at the same time maintaining low pressure contact with the inner surface of the retina. One portion 20 of the cantilever is physically attached to the retina, while the remaining area 26 of the cantilever is held in contact with the retina by a restoring force which develops along the cantilever's length-wise axis in response its curvature when the cantilever is in place along the inner radius of the retina. With this scheme, the area of physical attachment to the retina is distanced from the rest of the cantilever, which supports, e.g., stimulating electrodes, whereby any damage caused to the neurons by the attachment will have no effect on the somewhat remote neurons under the rest of the cantilever—these neurons may be interfaced and, e.g., stimulated. The attachment portion 20 is thus suited for supporting various circuitry, e.g., data and input power processors, which are not directly involved in neuron stimulation, while the remaining area 26, being separated from this portion, ideally supports the stimulating electrodes for stimulating the retinal ganglion cells.

Depending on the practicality of accessing areas of the inner retinal surface, the cantilever structure may range from a few millimeters to 5 centimeters in length, and preferably between 0.5–2 centimeters in length. The width of the cantilever may be between 0.5 mm–1 cm, and should be about 2 mm; this width being determined by the two-dimensional curvature of the eye, because the cantilever spring element will only bend in one direction. The cantilever width does not need to be uniform along the cantilever length, however. For example, the cantilever may have a more narrow central region separating the attachment portion from the stimulating region. In addition, appropriate width contours along the length of the cantilever could be designed to produce a standard force magnitude along the length of the cantilever.

The restoring force exerted by the cantilever on the inner retinal surface is ideally prespecified using an appropriate cantilever geometry, thickness, and material. Examples of materials suitable for the cantilever include silicon, silicon nitride, silicon carbide, sapphire, diamond, or other materials which exhibit some flexibility and which may be processed to render them biocompatible. In addition, the materials should be compatible with microfabrication techniques. The specific choice of materials will dictate the thickness of the cantilever for providing uniform, low pressure on the retinal surface. If, for example, silicon is used as the cantilever material and silicone is used to encapsulate the cantilever, the silicon and silicone portions could both be between 2–40 μm-thick, with the silicon layer being ideally between 5–15 μm-thick and the silicone layer being ideally between 5614 25 μm-thick.

Given these geometric guidelines, the cantilever geometry is particularly specified to provide both an adequate retinal contact and a minimum amount of pressure on the retina. This pressure should ideally be below 10 mm Hg; the ganglion cells are adversely impacted by prolonged pressures above this level. For example, glaucoma is a significant cause of blindness which would result from elevation of intraocular pressure for an extended time.

In particular, the force of the cantilever against the retina should be slightly greater than only the weight of the cantilever assembly. In addition, the weight of the assembly is minimized to thereby minimize both static and dynamic forces, i.e., accelerations, due to movement of the eye. Use of low-density materials such as silicone achieve this minimized acceleration and also minimize gravity effects on the contact pressure.

The force of the tip of the cantilever opposite the attachment portion may be determined as follows:

$$p = \delta E b h^3 / 4L^2$$

where p=force
E=Young's modulus
b=cantilever width
h=cantilever thickness
L=cantilever length
δ=deflection of tip from unbent position By selection of the cantilever geometry and area, a, the pressure, p/a, may be precisely and predictably specified for a particular material. The shape of the cantilever may be varied to precisely tailor the force along the length of the cantilever. This can be done using common numerical design modeling and simulation software packages to match the design goals of the cantilever with the shape of the eye and the preferred materials for the cantilever. Because pressure is a function of applied force per unit area, widening the structure in a particular area would tend to decrease the pressure in that local area.

As discussed above, the cantilever supports electrodes for stimulating ganglion cells in a location distant from the site of cantilever attachment to the retina. Such electrodes may be of any suitable design which would provide electrical current stimuli to the ganglion cell bodies. An array of electrodes may be positioned on one end 26 of the cantilever 10. Each electrode is connected via, for example, conducting traces, to circuitry 38 located at the attachment end 20 of the cantilever. As discussed above, the circuitry 38 may include pulse generation and power circuitry. The circuitry and electrodes may be discrete electronic pieces which are assembled on the cantilever, or they may be fabricated as an integrated body with the cantilever. Using a discrete assembly process, flip chip bonding using one of a variety of well-known techniques is preferred because such a method would minimize the overall mass of the cantilever structure.

Encapsulation of the cantilever, electrodes, and electronics is essential for biocompatibility of the structure with the retinal environment. Silicones have been demonstrated as a good choice for an encapsulation material based on their performance during direct immersion in saline environments. Silicones can be mixed to provide a wide range of mechanical properties, and can be micromachined in much the same manner as conventional electronic materials to a prespecified desired geometry. Fluorocarbons and polyesterimides may also be good encapsulation materials; their use with standard electronic materials, such as silicon dioxide, requires a silane coupling agent that could create stable bonds between these materials and silicon dioxide in an aqueous environment. Other biocompatible materials may also be selected as an encapsulation material.

Figure 3:
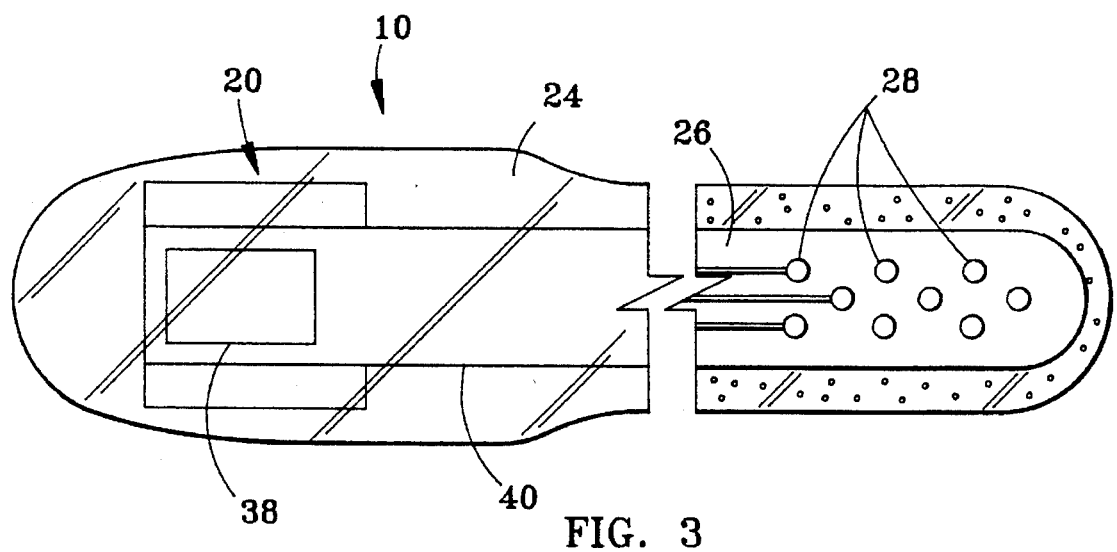
FIG. 3 is a planar view of the neural contact of the invention including an encapsulation layer.

As shown in FIGS. 2a, 2b, and 3, the encapsulation layer 24 surrounds the cantilever structure 40. This layer, preferably of silicone material, should be very flexible and soft, and should extend beyond the edges of the cantilever structure 40 by an amount equal to at least its thickness, and more preferably 4–5 times its thickness. The overhanging area may be perforated to allow residual vitreous to ooze through and hold it stable once it is in place on the retina. This is particularly advantageous as it is crucial to maintain a precise positioning of the contact structure. The silicone overhang edge also has the advantage of being better matched to the mechanical impedance with the neural tissue, and thereby minimizes the trauma or damage which the structural edges may cause to the retinal surface.

Referring specifically to FIG. 2b, the silicone layer is thickest at the point of attachment to the retina, and tapers away from the attachment area to the electrode area. The encapsulated cantilever structure may be attached to the retinal inner surface via conventional attachment techniques, such as using retinal tacks. Other suitable techniques may also be employed to physically anchor the attachment portion of the cantilever to the retinal surface.

Figure 4:
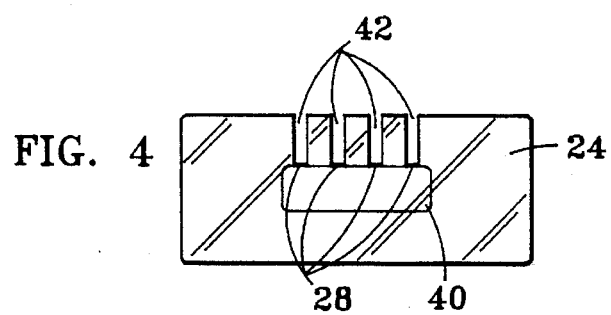
FIG. 4 is a side view of the neural contact of the invention including an encapsulation layer.

As shown in FIG. 4, the encapsulation layer includes channels 42 over each of the cantilever electrodes 28. The encapsulation layer channels act to recess the electrodes and provide further lateral confinement of the electrodes fields, because the encapsulation layer material is insulating. The encapsulation layer is ideally as thick as the diameter of one electrode, about 25 mm. The recessed design ensures that the equipotential lines corresponding to the electrode electric field are parallel to the surface of the electrode, providing for uniform current distribution on the electrode surface. The recess design might also limit the accumulation of electrochemical products that may be toxic to neurons and corrosive to the electrodes.

A silicon cantilever structure may be fabricated with the electrodes described above integrated with the cantilever, using standard electronic fabrication techniques. Beginning with a silicon wafer (not shown), p+ boron is diffused into the wafer in the desired lateral shape for the cantilever structure 40. The deep p+ layer acts as an etch stop for bulk micromachining of the cantilever structure once the electrodes are defined on the structure. Such bulk micromachining is preferably accomplished using an Ethylene Diamine Pyrocatechol (EDP) selective etch at the end of the fabrication process, as described below. Alternatively, the backside of the silicon wafer may be ground to thin the wafer prior to the fabrication sequence.

Electrodes and any desired signal processing circuitry may then be fabricated on the doped silicon wafer using standard microfabrication techniques to define the electrode structure, the circuitry components, and electrical interconnections.

Silicone elastomer (for example, Dow Corning MDX-4-4210) is then spun onto the wafer to form a 20–25 μm-thick layer, and is given a minimal cure. Then the silicone is masked and etched to define and expose the electrode contact opening and device cut out areas. This is achieved using standard masking and etching processes suitable for silicone. Once the patterning is complete, the wafer is then baked thoroughly according to the standard cure cycle for the chosen silicone. The entire wafer is then immersed in standard EDP to etch back the silicon substrate up to the p+ etch stop. The EDP only slowly degrades the silicone layer. As individual cantilever structures break free in the etch bath, they are removed and cleaned in phosphoric acid to remove any masking layer remaining on the silicone surface.

Many alternate fabrication processes are equally viable, based on particular choices for the cantilever structural material and the encapsulation material. For example, if silicon nitride, carbide, or diamond were chosen as the cantilever structural material, that material would be deposited on an oxidized silicon wafer via PECVD techniques.

Here there is no need for a bulk micromachining etch stop layer. The electrode interconnections and electrodes are then fabricated using a standard microfabrication process. Then a 6 micron-thick PECVD silicon nitride layer is deposited on the electrodes. The entire structure is patterned down to the silicon substrate using standard plasma etch processes for the nitride and oxide layers. Silicone is then deposited and patterned as described above. Finally, the entire silicon substrate is etched away in, e.g., EDP, to produce the finished cantilever structure.

Figure 5:
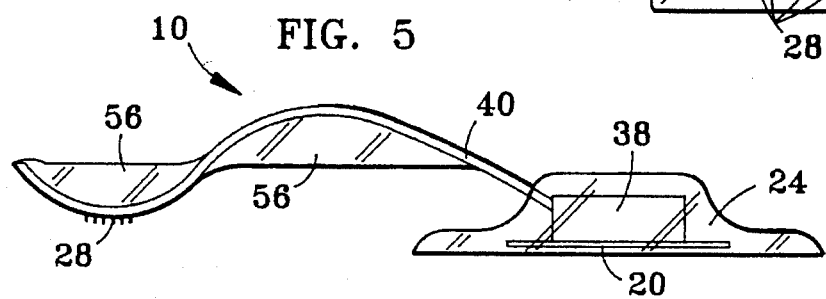
FIG. 5 is a side view of a second embodiment of the neural contact of the invention.

Referring to FIG. 5, the cantilever structure as described above is inherently straight due to the intrinsic mechanical properties of the most suitable materials, like silicon and silicon nitride. However, the cantilever 40 may be prebent into any desired bend or number of bends by casting a silicone rib into the structure. Alternatively, the structure may be held in a prebent position using silicone strap structures 56. This scheme is useful to make surgical placement of the structure easier and to avoid "digging" in of the end of the cantilever in the retinal tissue. An important advantage of this feature is that it bends the cantilever so as to contact the retina tissue only at a prespecified location, e.g., the location of an electrode array, and is out of contact over the tissue between the attachment point and the electrode array. This would be important in applications in which it is undesirable to contact a large area which might compromise regional blood supply.

In an alternate construction of the cantilever implant, multiple cantilevers may be attached together at one central attachment site, with each cantilever branching from this site. Each cantilever may support electronics and electrodes as described above. In another alternative scheme, several cantilevers may be individually attached at various locations over the inner surface of the retina.

Other embodiments for the low pressure neural contact structure are within the scope of the invention. Suitable structure geometries should ideally be capable of carrying various stimuli or recording electronics and electrodes. Furthermore, the site of attachment of the structure to the retina should be distanced from the site of active neural interface. Power and signal processing circuitry, which may mechanically compromise the neural tissue, should be relegated to the remote attachment site. And optimally, the contact structure should ensure that any stimulating electrodes are pressed against the retina with a known degree of pressure that remains constant despite variations in surgical procedure, despite variations in the strength of the contact attachment to the retina, and despite flexing, deformation, growth and aging of the eyeball.

The low-pressure contact and electrode designs of the invention are useful for any neural stimulation or sensing application in which neural tissue surface contact is required. The contact structure provides both the contacting surface and mechanical support of stimuli and sensory electronics and electrodes. Furthermore, the structure provides the ability for attachment to neural tissue in a location distant from an active stimulation location, thereby isolating any physiological degradation due to the attachment. And of equal importance, the contact structure inherently provides adequate surface pressure for contacting neural tissue, while at the same time minimizing that pressure due to its ability to easily conform to contours in neural tissue.

Thus, the contact structure of the invention is applicable to a wide range of stimulation prosthetics for visual, auditory, and sensory systems. The contact structure may in fact provide a unitary device for both stimulation and sensory electronics to stimulate neural tissue and record the neural response to that stimulation. The contact may also be used for functional electrical stimulation of the spinal cord neurons, ganglia for bladder activation, dorsal root ganglion neurons, and autonomic nerves such as the vagal nerve, for treating epilepsy, or activation of paretic limbs, or in treatment for impotence. Furthermore, the contact structure may be used in an implantable system for use in physiological studies of various sensory systems. The contact may also be employed as a sensory system to measure chemical and physical parameters like oxygen, carbon dioxide, pH, calcium, glucose, or temperature and pressure, and may provide an implantable mechanism for use as a chemical dispersement system to disperse chemicals into the nervous system.

We claim:

1. A low-pressure neural contact structure for contact with neural tissue of the retina within which are ganglion cells to be electrically stimulated comprising:

a first portion for attachment to a first location on an inner surface of the retina, and a second portion interconnected with said first portion via an interconnection adapted to contact a second location on the inner surface of the retina adjacent to said ganglion cells to be stimulated, said interconnection easily conforming to contours in said neural tissue to exhibit a weak restoring force in response to curvature of the interconnection along an inner radius of the retina to provide a desired pressure of contact of said second portion against said neural tissue of below 10 mm mercury, the desired pressure sufficient to permit stimulation of the neural tissue without damage to said neural tissue.

2. The neural contact of claim 1 wherein said first and second portions together comprise an integral structure.

3. The neural contact of claim 2 wherein said integral structure is of a generally rectangular geometry.

4. The neural contact of claim 3 wherein said integral structure comprises a cantilever.

5. The neural contact of either of claims 1 or 4 wherein said second portion provides mechanical support for a stimulating electrode structure positioned on said second portion for stimulating said ganglion cells.

6. The neural contact of claim 4 wherein said cantilever comprises silicon.

7. The neural contact of claim 6 wherein said second portion of said cantilever comprises an array of stimulating electrodes for stimulating said ganglion cells.

8. The neural contact of claim 7 further comprising an encapsulation layer of biocompatible material which encapsulates said cantilever.

9. The neural contact of claim 8 wherein said encapsulation layer comprises silicone.

10. The neural contact of claim 8 wherein said encapsulation layer overhangs edges of said cantilever.

11. The neural contact of claim 9 wherein said encapsulation layer material in the location of said first portion is thicker than said encapsulation layer material in the location of said second portion.

12. The neural contact of claim 10 wherein said encapsulation layer material in the location of said edges of said cantilever comprises perforations.

13. The neural contact of claim 9 wherein said encapsulation layer comprises an array of channels located at a position over said second portion corresponding to said array of stimulating electrodes.

14. The neural contact of claim 9 wherein said cantilever is between 2–40 microns-thick.

15. The neural contact of claim 14 wherein said cantilever is between 5–15 microns-thick.

16. The neural contact of claim 14 wherein said cantilever is between 2 mm–5 cm-long.

17. The neural contact of claim 16 wherein said cantilever is between 0.5–2 cm-long.

18. The neural contact of claim 16 wherein said cantilever is between 0.5 mm–1 cm-wide.

19. The neural contact of claim 18 wherein said cantilever is between 1–3 mm-wide.

20. The neural contact of claim 14 wherein said encapsulation layer is between 5–25 microns-thick.

21. The neural contact of claim 9 further comprising a silicone rib positioned on said cantilever to bend said cantilever in a predetermined geometric shape.

22. The neural contact of claim 7 wherein the width of said cantilever in the location of said first portion and in the location of said second portion is greater than the width of said cantilever in the location of said interconnection.

* * * * *

UNITED STATES PATENT AND TRADEMARK OFFICE
CERTIFICATE OF CORRECTION

PATENT NO.  : 5,476,494
DATED       : December 19, 1995
INVENTOR(S) : David J. Edell, et. al.

It is certified that error appears in the above-indentified patent and that said Letters Patent is hereby corrected as shown below:

After the title, please insert the following paragraph: -- This invention was made with government support under Conttact Number F19628-90-C-002 awarded by the Air Force. The government has certain rights in the invention. --

Signed and Sealed this

Twenty-seventh Day of August, 1996

Attest:

BRUCE LEHMAN

Attesting Officer

Commissioner of Patents and Trademarks